United States Patent [19]

Ropiak et al.

[11] Patent Number: 5,779,693

[45] Date of Patent: *Jul. 14, 1998

[54] FLEXIBLE PLASTIC CONTAINER FOR THE CONTAINMENT AND DELIVERY OF DIAGNOSTIC CONTRAST MEDIA AND PARENTERAL DRUG FORMULATIONS

[75] Inventors: Irene K. Ropiak, Somerset; John J. Niedospial, Jr., Burlington, both of N.J.

[73] Assignee: Bracco Diagnostics, Inc., Princeton, N.J.

[*] Notice: The term of this patent shall not extend beyond the expiration date of Pat. No. 5,728,086.

[21] Appl. No.: 739,440

[22] Filed: Oct. 29, 1996

Related U.S. Application Data

[63] Continuation-in-part of Ser. No. 692,813, Jul. 30, 1996, Pat. No. 5,738,671.

[51] Int. Cl.⁶ .................................................. A61B 5/00
[52] U.S. Cl. ................................. 604/408; 604/414
[58] Field of Search ........................... 604/403, 408, 604/409, 411, 412, 414, 416; 206/419, 420

[56] References Cited

U.S. PATENT DOCUMENTS

| | | |
|---|---|---|
| Re. 32,065 | 1/1986 | Ralston et al. . |
| 331,039 | 11/1885 | Davis ........................... 604/408 |
| 4,088,166 | 5/1978 | Miller . |
| 4,892,537 | 1/1990 | Carmen et al. . |
| 4,976,707 | 12/1990 | Bodicky et al. . |
| 4,978,579 | 12/1990 | Rosenbaum ................ 428/483 |
| 5,088,994 | 2/1992 | Porat . |
| 5,289,858 | 3/1994 | Grabenkort ................ 604/403 |
| 5,385,564 | 1/1995 | Slater et al. ............... 604/416 |
| 5,423,794 | 6/1995 | Adolf et al. . |

Primary Examiner—Mark O. Polutta
Assistant Examiner—David J. Cho
Attorney, Agent, or Firm—Imre Balogh

[57] ABSTRACT

Flexible medical fluid container made from first and second flexible plastic sheets sealed together at their periphery to form a pouch defining an interior. The bottom portion of the container terminates in a first angle and a second angle of from 5° to 45° to facilitate the flow of medical fluid towards an access port. Portions of the interior of the pouch is embossed in a V-shaped configurations to direct flow of fluid towards the access port.

13 Claims, 16 Drawing Sheets

FLEXIBLE PLASTIC CONTAINER FOR THE CONTAINMENT AND DELIVERY OF DIAGNOSTIC CONTRAST MEDIA AND PARENTERAL DRUG FORMULATIONS

This is a continuation-in-part of application Ser. No. 08/692,813, filed on Jul. 30, 1996 now U.S. Pat. No. 5,738,671.

BACKGROUND OF THE INVENTION

1. Field of the Invention

This invention relates to flexible plastic containers, such as bags and bottles, for the containment and delivery of fluids. More particularly the invention relates to flexible plastic containers for the containment and delivery of parenteral solutions including diagnostic contrast media, nutrients and drug formulations.

2. Reported Developments

Prior to the discovery and development of polymeric materials, parenteral liquids have been supplied to hospitals exclusively in glass bottles. The disadvantages of glass bottles, such as cost, shipping, storage and disposal, prompted the prior art to provide flexible, sterilizable containers in the forms of bags and bottles for the containment and delivery of parenteral solutions, such as diagnostic contrast media, nutritional and drug formulations. Such containers typically comprise: a flexible plastic sheet formed into a pouch, bag or bottle shape filled with a solution inside therein in a sterile environment; and one or more ports to fill and/or access the solution. Flexible tubing is also provided one end of which is connectable to a port on the container, and the other end connectable to a syringe or catheter pre-inserted into the site of delivery on the patient. Control means are also usually included with the tubing, such as valves and clamps for initiating, controlling and terminating the flow of the liquid to the delivery site. The container, tubing and control means are sterile packaged ready for use.

One of the requirements to be satisfied in flexible containers for delivering parenteral solutions to patients is that by their construction and design they deliver their total contents in a uniform, steady manner and without retaining liquid drops on their walls. By meeting such requirement the medical practitioner can determine the amount of parenteral solution delivered from the container to the patient. The prior art has addressed this requirement, as shown for example in U.S. Pat. No. 4,892,537, which discloses a bag having substantially parallel major sides or edges and converging minor sides which meet at a point forming an obtuse angle of at least 110°. The converging edges are designed to guide the filled bag contents in a substantially unobstructed manner in a funnel-like fashion to an exit port.

U.S. Pat. No. 4,088,166 also addresses the problem of incomplete and non-uniform collapse of parenteral solution containers. The incomplete collapse is attributed to the stiffness of the thin-walled polypropylene container which tends to resist collapse to such a degree that the moderate suction pressure exerted on the container by weight of the parenteral solution is insufficient to cause its complete collapse. The non-uniform collapse, on the other hand, is attributed to the observed facts that on some occasions, the bags collapse along the long axis of their cross section, while on other occasions they tend to collapse along both the short axis of the cross-section as well as the long axis. As a result, the medical practitioners cannot determine exactly how much parenteral solution has been delivered out from the container. In order to solve the problem of incomplete and non-uniform delivery, the patentee incorporates gusset portions in the body portion of the container adjacent the shoulder portion. The gusset portions include lines of flexing weakness to facilitate the collapse of the container adjacent the shoulder portion as the contents thereof are withdrawn. The gussets said to facilitate both the lateral and longitudinal collapse of the container as it is emptied.

Medical practitioners have also observed fluid "hold up", i.e., when drops of parenteral solutions tend to remain on the internal walls of the flexible container as the solution is being delivered to the site of administration. The moderate suction pressure exerted on the walls of the container is insufficient to overcome the force existing between the drops of liquid and the walls of the container. Often, as the container is being drained, the emptied portion of the parallel walls adhere to each other further trapping drops of the liquid. As a consequence, the prescribed amount of parenteral solution is not delivered to the patient. Such delivery, especially in traumatic circumstances where a precise amount of a drug must be delivered into the patient, can make the difference between life and death of the patient.

The present invention addresses the problems associated with the lack of complete delivery of content, such as incomplete and non-uniform collapse of the container during administration of the parenteral solution, and hold up of drops of the solution on the walls of the container. The present invention provides means by which the parallel walls of the container are spaced apart from each other by having all or at least portions of the walls embossed which due to low coefficient of friction allows relative movements of the walls and prevents sticking.

The present invention also provides for easy access to the parenteral solution contained in the flexible container, its maintenance therein, and its controlled delivery to the patient.

Further, the present invention provides a unitary container having control and delivery means integral with the container requiring no assembly prior to use. Such a unitary container is especially suited for use in both hospital and field emergency situations where assembly of prior art devices, having a bag, tubing, extension tubing, needle and catheter are individually packaged in a kit, would require considerable time prior to use.

SUMMARY OF THE INVENTION

The present invention is directed to a flexible, unitary plastic container, such as a bag, pouch or bottle, for the containment and delivery of parenteral solutions, such as diagnostic contrast media, nutrients and drug formulations to a patient in need of such parenteral solutions.

The flexible plastic container may be of any configuration, such as, square, round, oval, hexagonal or octagonal. Typically, it is a generally rectangular configuration which will be described hereunder.

The container comprises:

a) first and second flexible plastic sheets having a generally rectangular configuration superimposed and sealed together at their periphery to form a pouch defining an interior, said pouch having a top and a bottom portion; said bottom portion terminates in a first angle and a second angle of from about 5° to about 45°, preferably of from about 10° to about 30°, and most preferable from 10° to 20° from the center of said bottom portion and relative to a horizontal plane crossing the center of said bottom portion to direct and facilitate the flow of content of the solution contained in the pouch towards an access port; all or at least portions of said interior of said pouch being mechanically deformed to prevent adhesion of said first and second plastic walls;

b) an access member integral with said pouch located at the center of the bottom portion of said pouch for allowing filling of the container with a parenteral solution and access thereto for its delivery, said access member comprising:

1) an access port located below the bottom portion of said pouch where said first angle and said second angle meet; and 2) a flexible tubing one end of which is integral with said access port and the other end of which is removably covered with a cap; said flexible tubing being equipped with a one way luer slip lock assembly with a vent for controlling the delivery of the parenteral solution from the container.

The one-way luer slip stopcock assembly with vent may be positioned at the open end just below the removable cap, or it may be positioned next to and adjacent to the port.

Preferably the top portion at the periphery of the container comprises at least one hole for suspending the container when it is in use for delivering the content thereof to the delivery site.

Preferably the bottom portion at the periphery of the container comprises at least one, and preferably a plurality, of holes to facilitate suspending the container during the filling process.

Additional features and advantages of the present invention will be apparent from the drawings and of the detailed description.

DETAILED DESCRIPTION OF THE INVENTION

Figure 1:
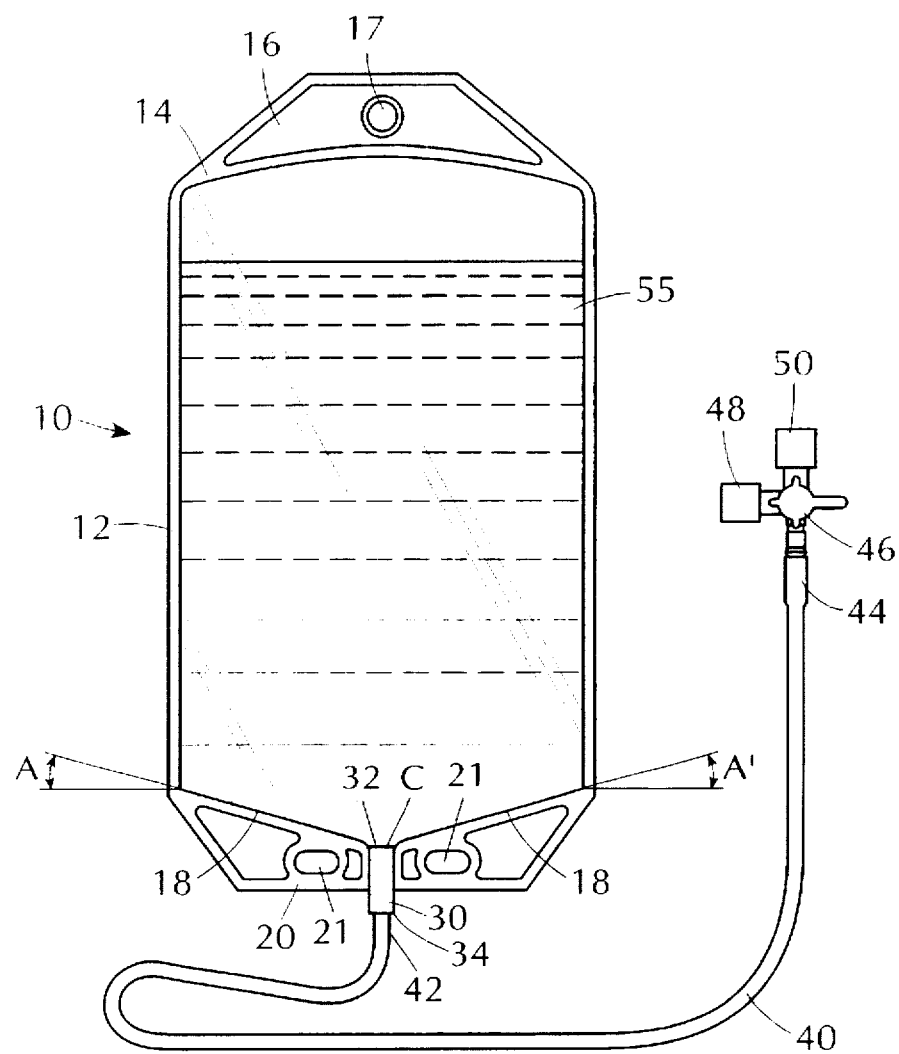
FIG. 1 is a plan view of the flexible container in accordance with the present invention showing an access port, and a tubular access member; said tubular access member having a cap, and luer slip stopcock assembly with vent at the open end of the access member.
Figure 2:
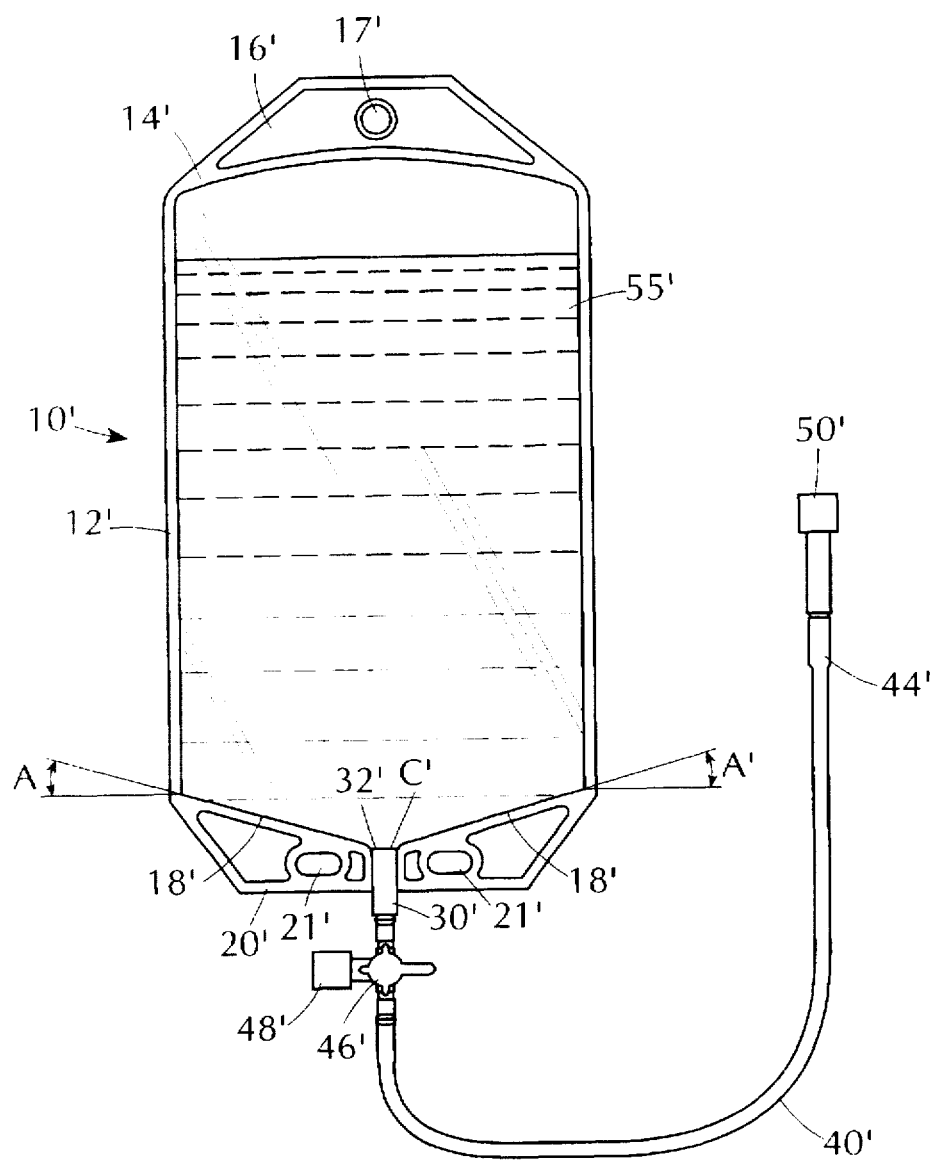
FIG. 2 is a plan view of another embodiment of the flexible container in accordance with the present invention showing the access port and the tubular access member; said tubular access member having cap at the open end thereof, and luer slip stopcock assembly with vent positioned next to and adjacent to the access port.

The present invention provides a flexible plastic container, in the shape of a bag, pouch or bottle, for the containment and delivery of diagnostic contrast media, nutrients and drug formulations. In the drawings where like numerals indicate like elements or portions, the reference character 10 and 10' in FIGS. 1 and 2 indicate the container which, in a preferred embodiment, is a pouch-like device, comprising two superimposed sheets of suitable length and width made of flexible or pliable materials, such as polymeric materials including polyethylene, polypropylene, and preferably thermoplastic materials. The superimposed sheets forming the pouch-like container are preferably made of transparent materials so as to allow observation of the amount of its content prior to and subsequent to the filling sterilization operation and delivery thereof to the patient. Each of the superimposed transparent sheets is preferably formed of multilayers of laminated thin films at least one of which constitutes a barrier which is impervious to atmospheric gases, moisture and bacteria. The superimposed sheets are preferably mono or multilayer flat welded to each other so as to form the pouch whose volume is zero before it is filled with a parenteral solution. When the pouch is filled or partially filled as shown by 55 in FIG. 1 and 55' in FIG. 2, it assumes the shape of a small cushion. The superimposed sheets are joined together along marginal areas 12, 12', 14, 14', 16, 16', 18, 18', 20 and 20' as shown in FIGS. 1 and 2 respectively.

Reference to embodiment of one of the present invention will be made by numerals without superscripts, while reference numerals with superscripts will relate to the second embodiment of the present invention.

The bottom portion of pouch 10 or 10' terminates in first angle A and second angle A' from the center C or C' of said bottom portion and relative to a horizontal plane crossing the center C or C' of said bottom portion to direct and facilitate the flow of content contained in the pouch towards an access port. Angles A and A' are of from about 5° to about 45°, preferably from 10° to 30° and most preferably form 10° to 20°.

An access port 30 or 31' located at center C or C' of the bottom portion of pouch 10 or 10' is sealed between the first sheet and second sheet of the pouch comprising a top, liquid-contacting portion 32 or 32' and a bottom portion 34 or 34' to which a flexible tubing 40 or 40' i.e. intravenous (IV) line is permanently or fixedly attached by heat sealing or by any other means. Access port 30 or 30' serves for both the filling and for the delivery of the parenteral liquid. It is important that top portion 32 or 32' of access port 30 or 30' is located below a horizontal plane crossing the center C or C' of said bottom portion so that all the liquid content of the pouch can be drained into flexible tubing 40 or 40'.

Referring to FIG. 1, flexible tubing 40 is permanently or fixedly attached at one end 42 to access port 30 while at its other end 44 it is attached to a control means comprising: a one-way luer slip stopcock 46, vent 48, and cap 50.

In the other embodiment of the invention shown in FIG. 2, flexible tubing 40' is permanently or fixedly attached at one end 42' to access port 30', while at its other end 44' it is covered with removably attached cap 50'. In this embodiment control means comprising a one-way luer slip stopcock and vent, is located at end 42' of flexible tubing 40', adjacent to access port 30'.

Marginal areas 16 and 16' in FIGS. 1 and 2 preferably comprise at least one hole 17 or 17' for suspending the pouch when it is in use for delivering the content of the pouch to a delivery site.

Marginal areas 20 and 20' in FIGS. 1 and 2 preferably comprise at least one, and more preferably a plurality, of hole(s) 21 and 21' to facilitate suspending the pouch during the filling process.

It was suprisingly discovered that if the inside wall of the first sheet or the second sheet forming the pouch 10 or 10' is embossed, fluid hold up in the form of drops adhering to the inside walls can be reduced or eliminated and the walls, as the content of the pouch is being drained into the injection site, adhering together and further trapping drops of the fluid can be prevented. In accordance with this discovery there are provided the following preferred embodiments of the invention.

Figure 3A:
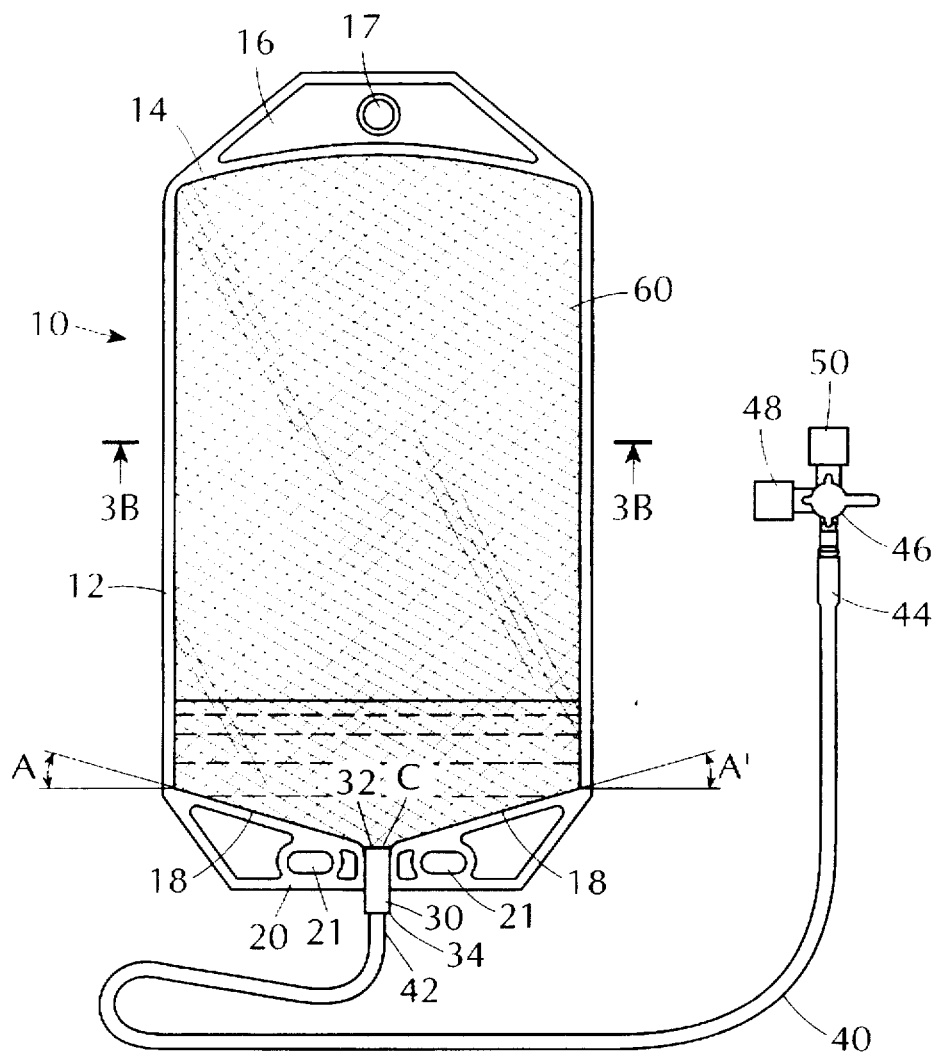
FIG. 3A is plan view of the flexible container shown in FIG. 1 one wall of which is embossed in a checkerboard fashion.
Figure 3B:
FIG. 3B is a cross-section of the flexible container shown in FIG. 3A taken along the line 3B—3B.

Referring to FIG. 3A and FIG. 3B, the inside wall of first sheet of pouch 10 shown in FIG. 1 is embossed in a checkerboard manner 60, the checkerboard consisting of squares the 90° angles of which pointing downward towards the center C of the pouch. The size of the individual squares may be in the range of from 0.01 to 10 $mm^2$ or larger. The size of the individual squares may vary the determination of which would be influenced by the viscosity and the surface tension of the parenteral liquid for the delivery of which the pouch is intended.

While the inside wall of both first sheet and second sheet may be embossed, it was observed that the pouch functions better in terms of eliminating fluid hold up and preventing the superimposed walls from sticking together when only one inside wall of the first or second sheet is embossed.

Figure 4A:
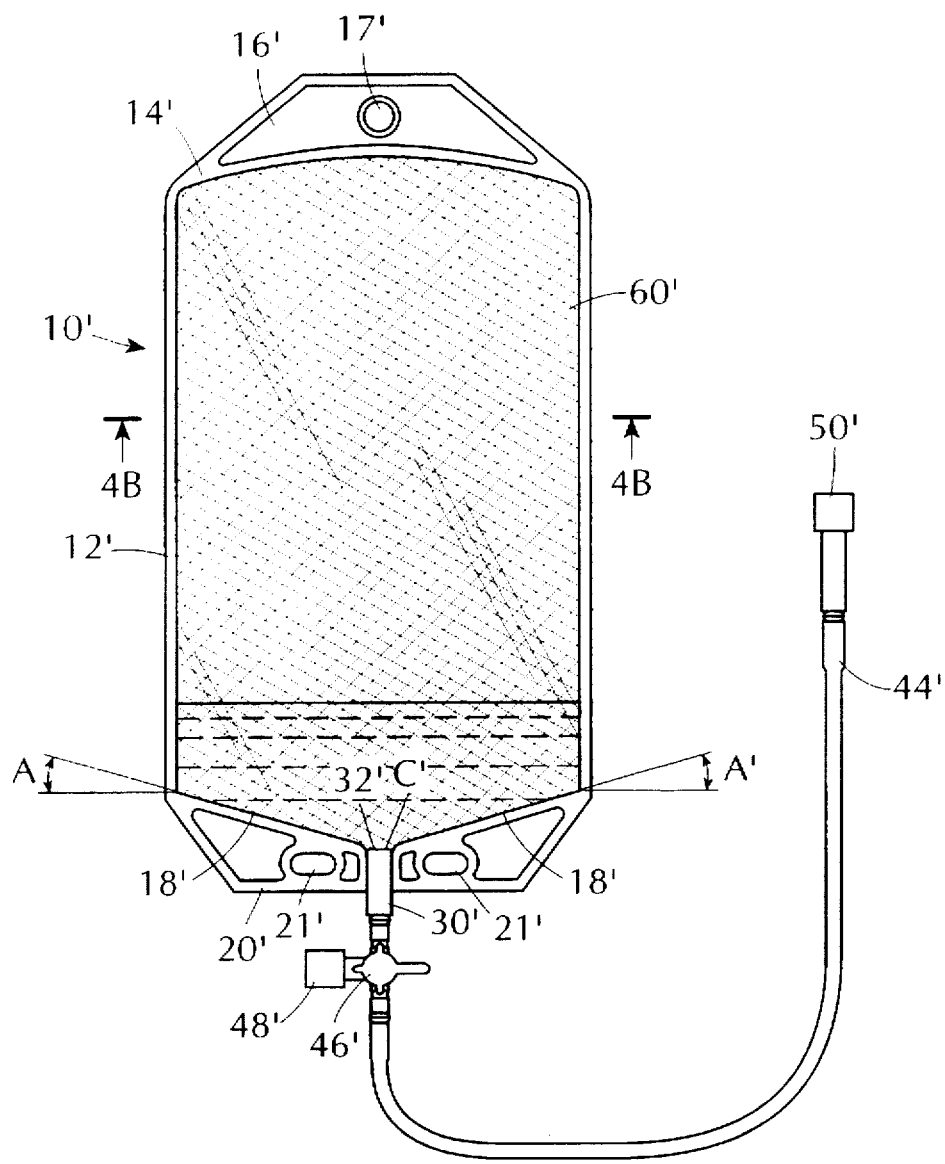
FIG. 4A is a plan view of the flexible container shown in FIG. 2 one wall of which is embossed in a checkerboard fashion.
Figure 4B:
FIG. 4B is a cross-section of the flexible container shown in FIG. 4A taken along the line 4B—4B.

FIG. 4A and FIG. 4B show the embodiment described in FIG. 2, except that the inside wall of first sheet of pouch 10' is embossed as described in FIGS. 3A and 3B.

Figure 5A:
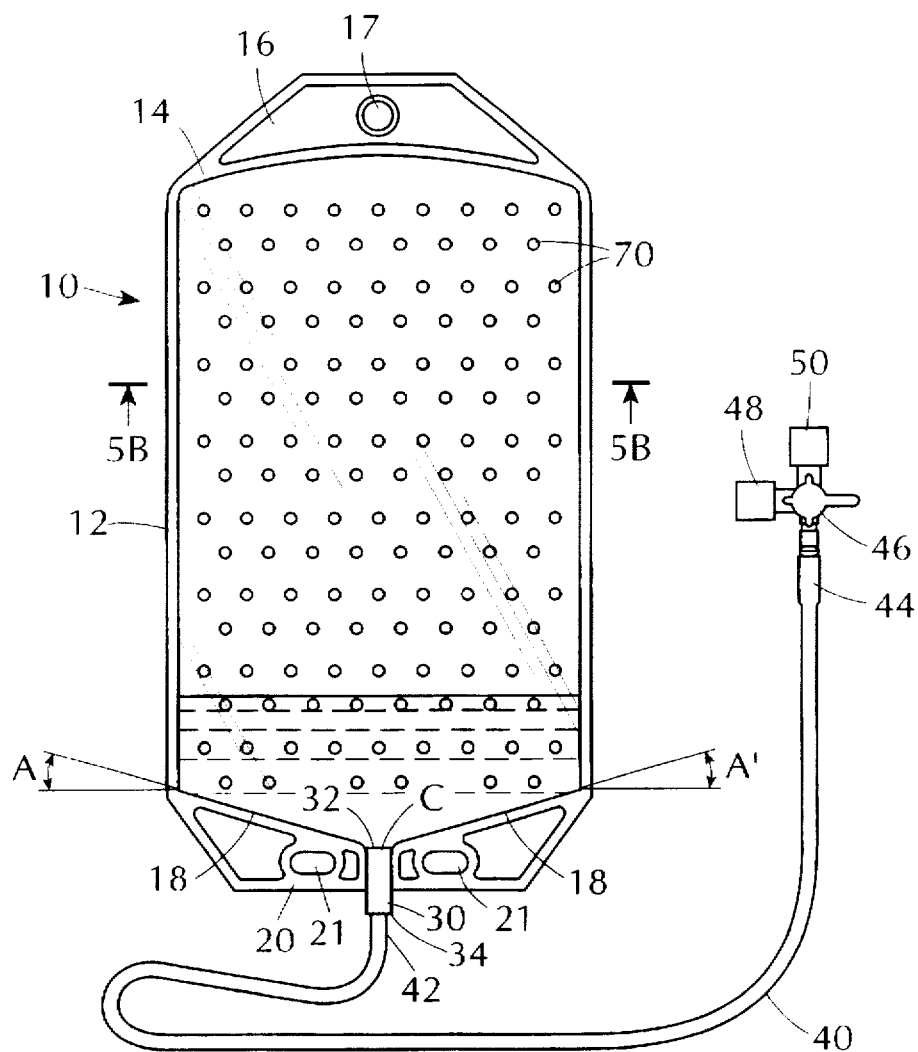
FIG. 5A is a plan view of the flexible container shown in FIG. 1 one wall of which is embossed in a dotted fashion.
Figure 5B:
FIG. 5B is a cross-section of the flexible container shown in FIG. 5A taken along the line 5B—5B.

Referring to FIG. 5A and FIG. 5B, the inside wall of first sheet of pouch 10 of FIG. 1 is embossed with dots or micro circles 70 in a spaced relationship from each other. The dots or circles may vary in diameter from 5 microns to several mms and may be spaced from each other of from about 10 microns to about 10 mms or longer. While both inside walls of the first sheet and second sheet may be embossed, it is preferred that only the first sheet or second sheet be embossed.

Figure 6A:
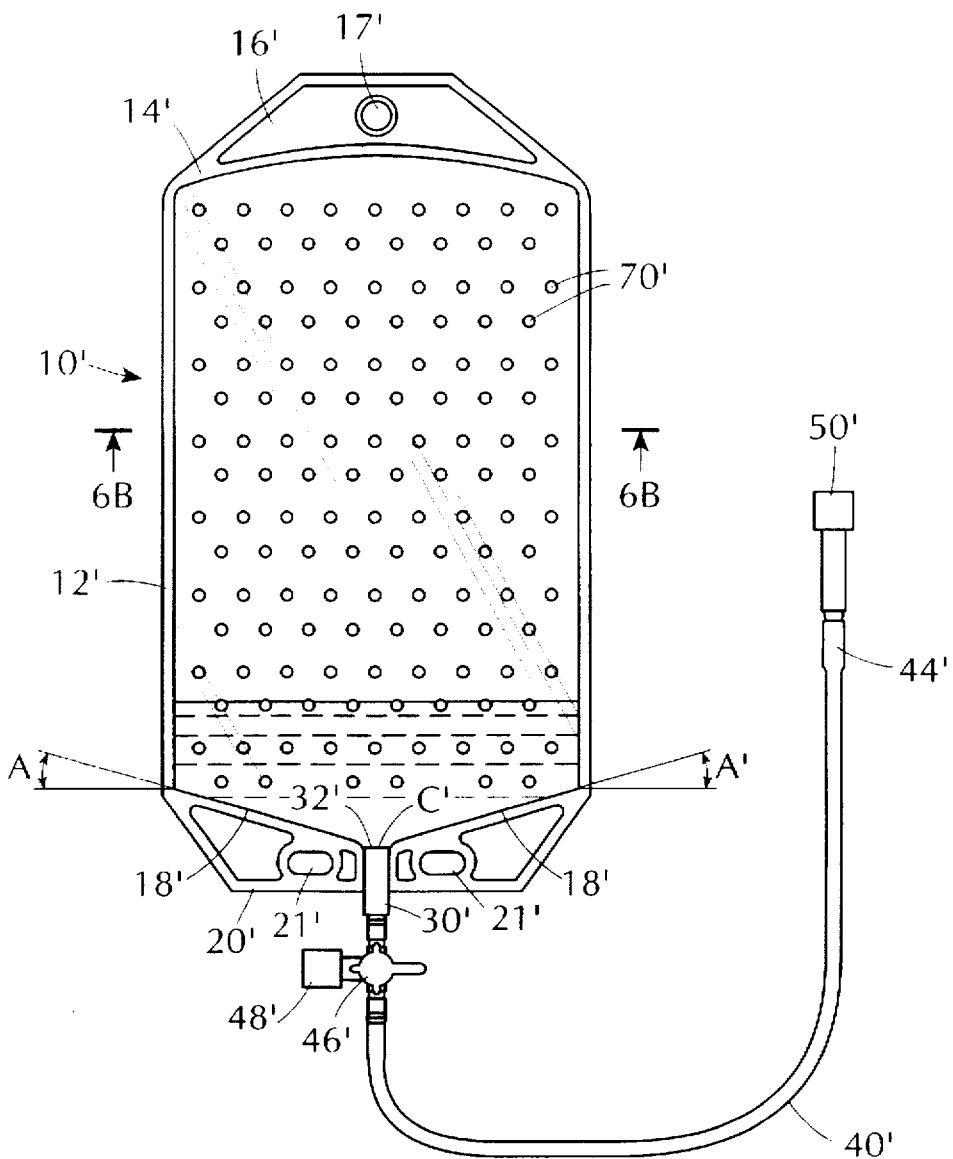
FIG. 6A is a plan view of the flexible container shown in FIG. 2 one wall of which is embossed in a dotted fashion.
Figure 6B:
FIG. 6B is a cross-section of the flexible container shown in FIG. 6A taken along the line 6B—6B.

FIG. 6A and FIG. 6B show the embodiment described in FIG. 2, except that the inside wall of first sheet of pouch 10' is embossed 70' as described in FIGS. 5A and 5B.

Figure 7A:
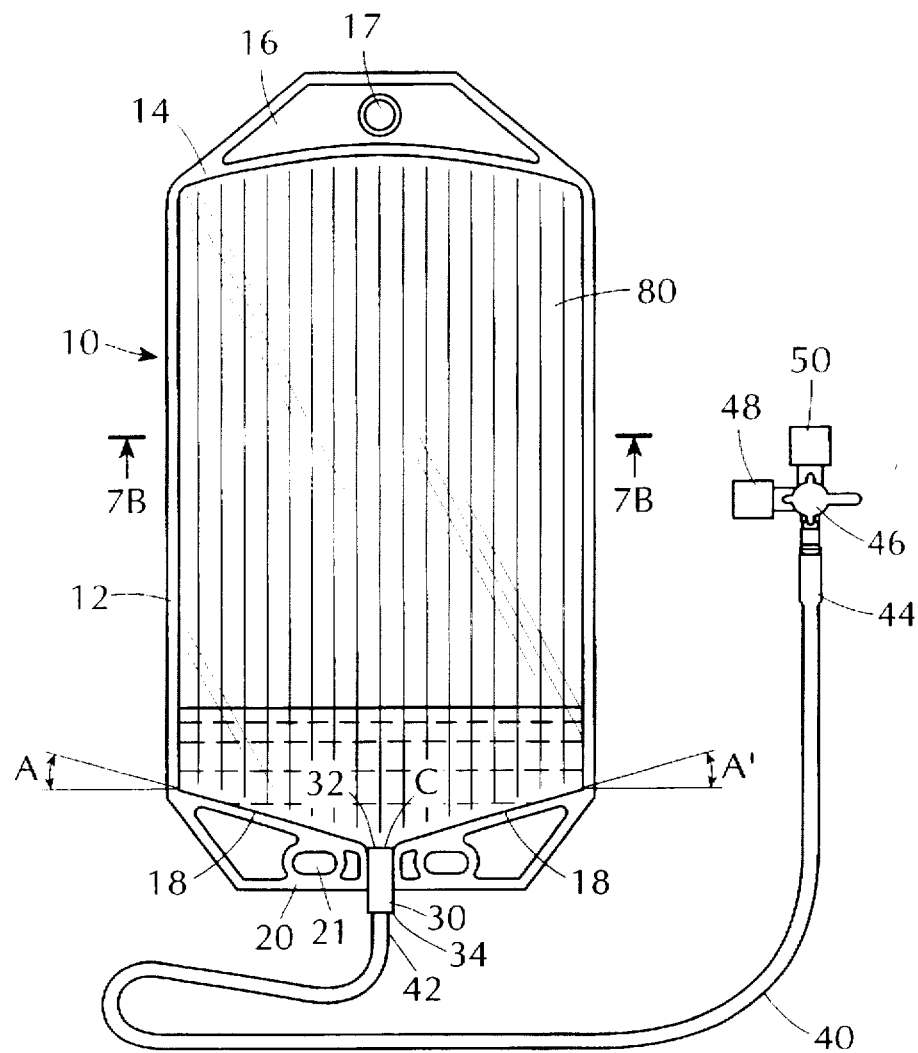
FIG. 7A is a plan view of the flexible container shown in FIG. 1 one wall of which is embossed with vertically oriented channels.
Figure 7B:
FIG. 7B is a cross-section of the flexible container shown in FIG. 7A taken along the line 7B—7B.

Referring to FIG. 7A and FIG. 7B, the inside wall of first sheet of pouch 10 shown in FIG. 1 is embossed 80 in vertical channel configuration in spaced relationship from each other. The width of the individual channels may be in the range of from about 0.01 to about 10 mm or larger. The channels may be spaced from each other of from about 10 microns to about 10 mms. While both inside walls of the first sheet and second sheet may be embossed, it is preferred that only one inside wall of the first or second sheet be embossed.

Figure 8A:
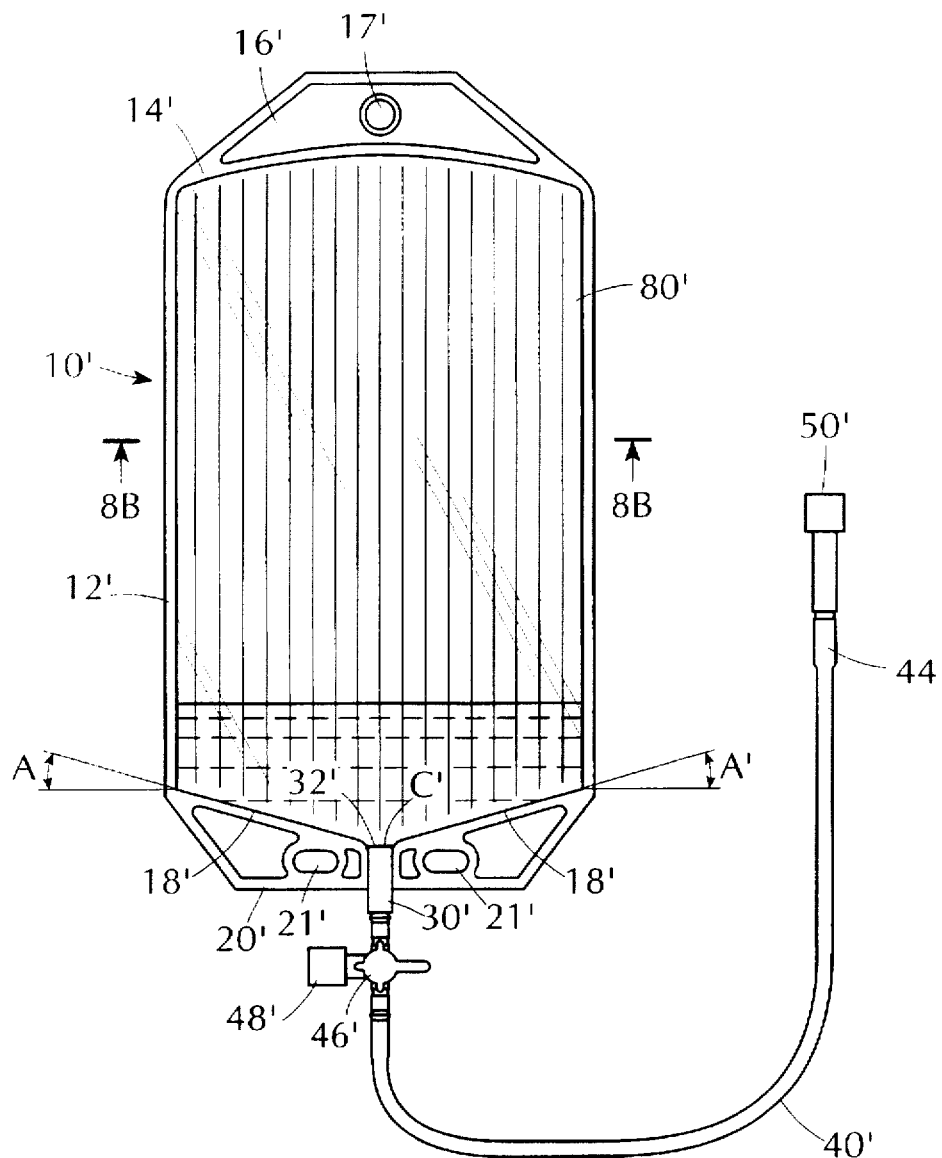
FIG. 8A is a plan view of the flexible container shown in FIG. 2 one wall of which is embossed with vertically oriented channels.
Figure 8B:
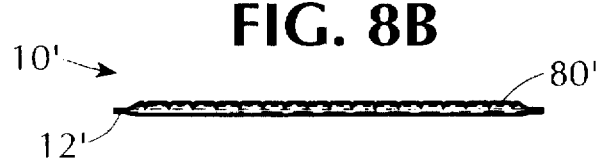
FIG. 8B is a cross-section of the flexible container shown in FIG. 8A taken along the line 8B—8B.

FIG. 8A and FIG. 8B show the embodiment described in FIG. 2, except that the inside wall of first sheet of pouch 10' is embossed 80' as described in FIGS. 7A and 7B.

Figure 9A:
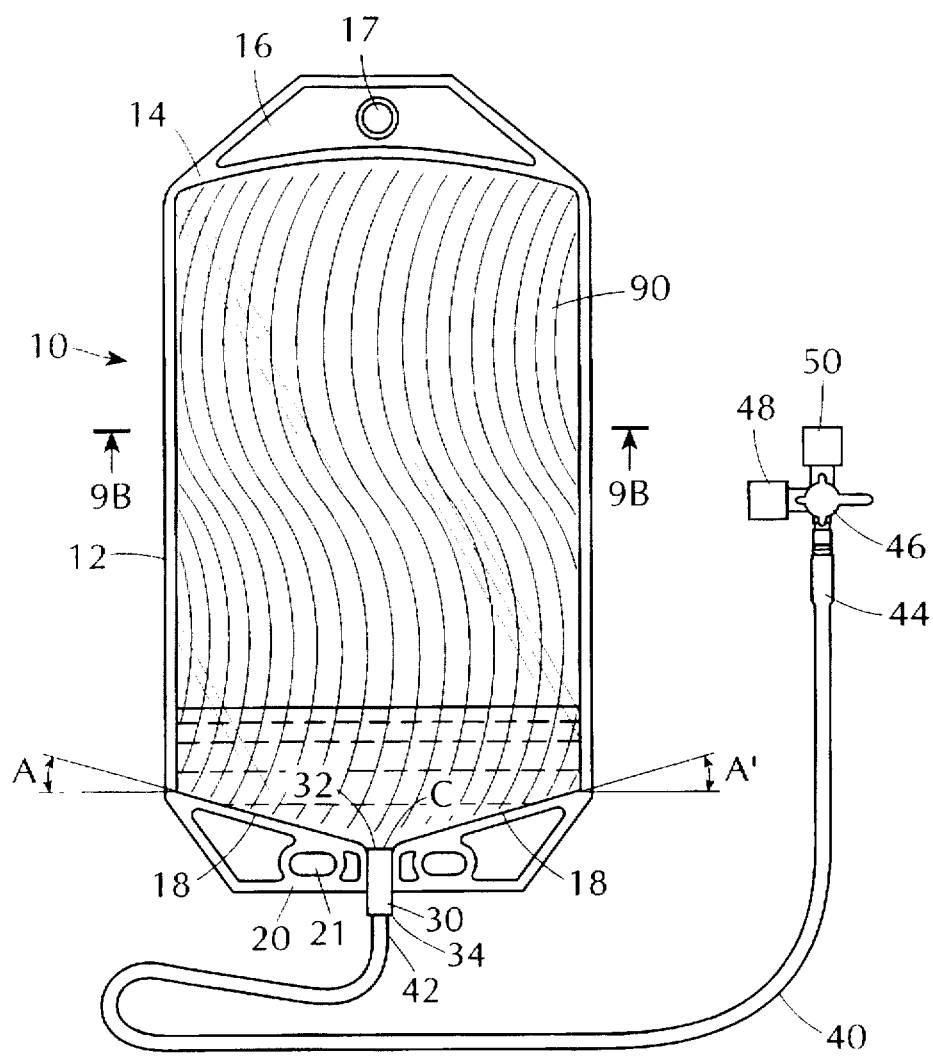
FIG. 9A is a plan view of the flexible container shown in FIG. 1 one wall of which is embossed with vertically oriented S-shape channels.
Figure 9B:
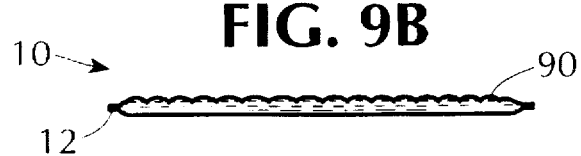
FIG. 9B is a cross-section of the flexible container shown in FIG. 9A taken along the line 9B—9B.

Referring to FIG. 9A and FIG. 9B, the inside wall of first sheet 90 of pouch 10 of FIG. 1 is embossed with vertically oriented channels which have a slight S-shape configuration in a spaced relationship from each other. The size of the width of individual channels may be in the range of from about 0.01 to about 10 mms or larger. The channels may be spaced from each other of from about 10 microns to about 10 mms. While both inside walls of the first sheet and second sheet may be embossed, it is preferred that only one inside wall of the first or second sheet be embossed.

Figure 10A:
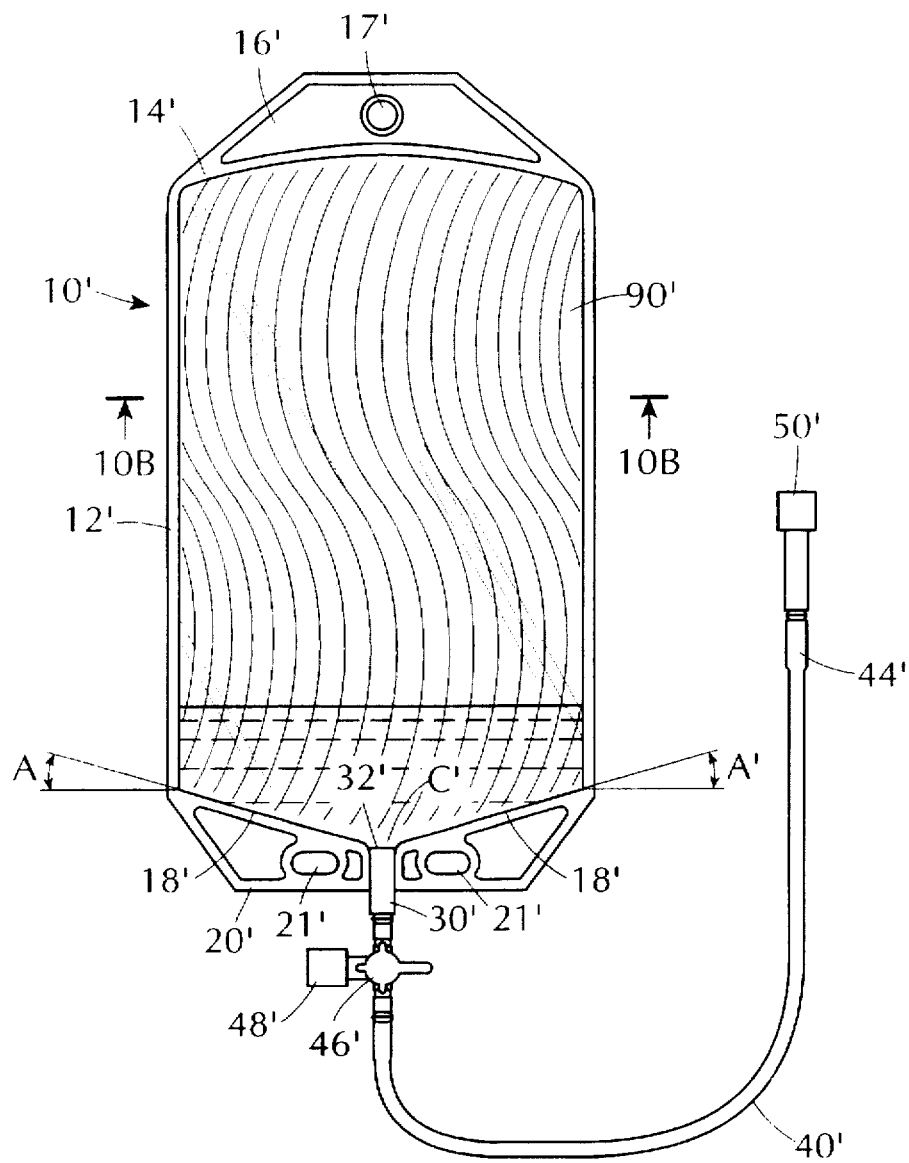
FIG. 10A is a plan view of the flexible container shown in FIG. 2 one wall of which is embossed with vertically oriented S-shape channels.
Figure 10B:
FIG. 10B is a cross-section of the flexible container shown in FIG. 10A taken along the line 10B—10B.

FIG. 10A and FIG. 10B show the embodiment described in FIG. 2, except that the inside wall of first sheet of pouch 10' is embossed 90' as described in FIGS. 9A and 9B.

Figure 11:
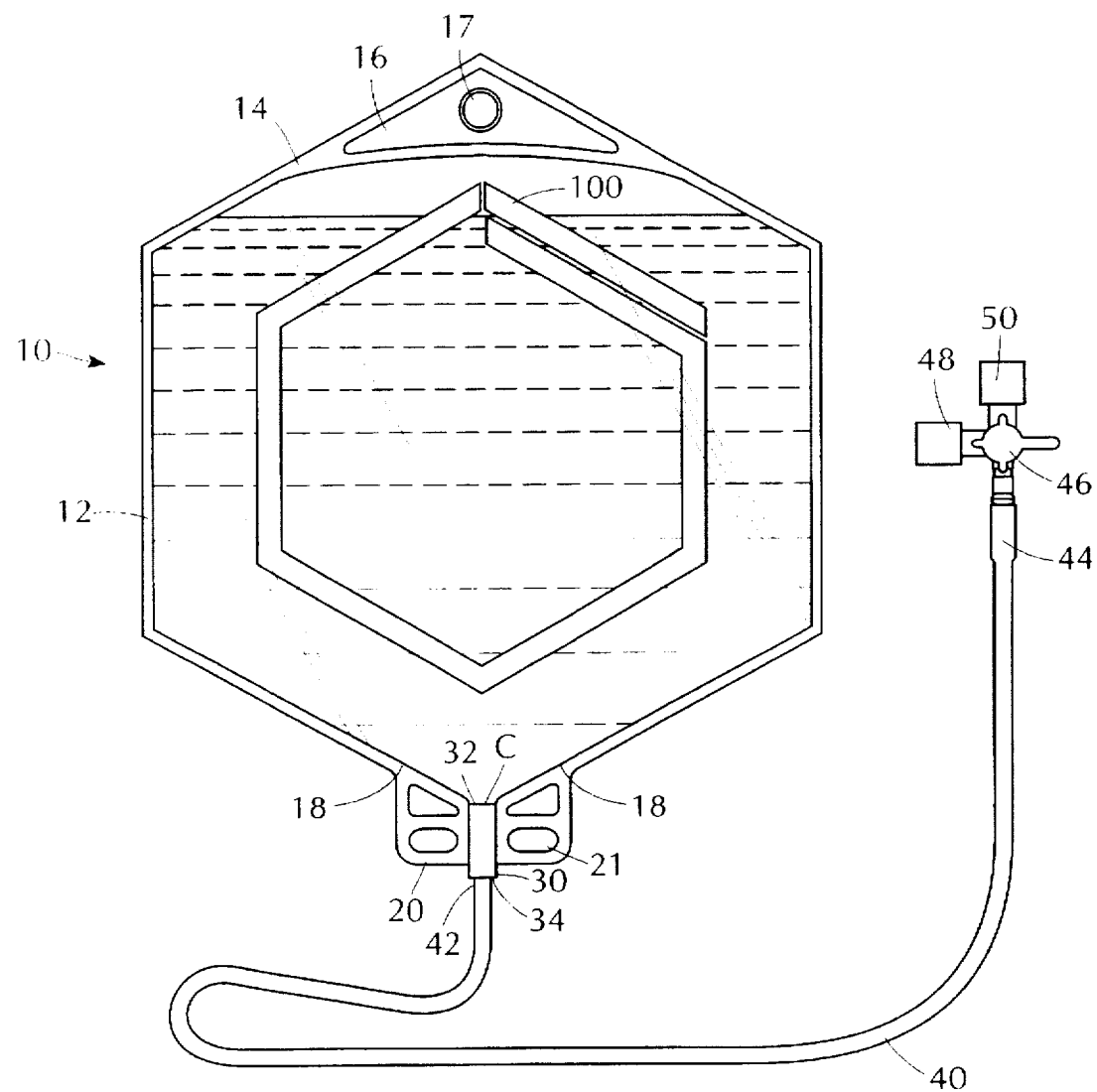
FIG. 11 is a plan view of the flexible container in accordance with the present invention having a hexagonal configuration showing an access port, and a tubular access member; said tubular access member having a cap, and a luer slip stopcock assembly with vent at the open end of the access member.

FIG. 11 shows a hexagonal configuration of the pouch shown in FIG. 1 wherein the numeral 100 illustrates a logo in the shape of a hexagon embossed on one sheet of the pouch or attached to the outside wall of the pouch.

Figure 12:
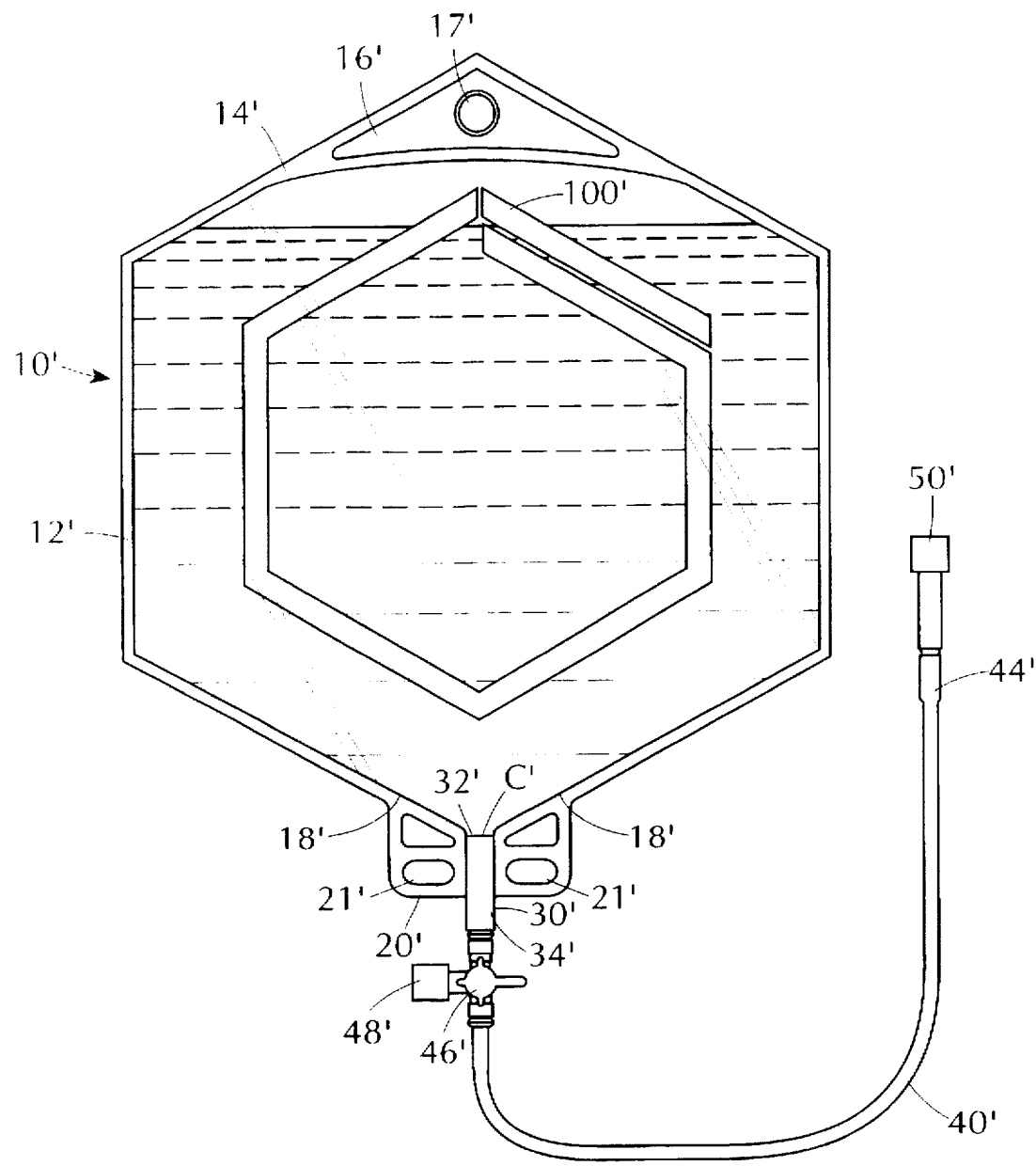
FIG. 12 is a plan view of the flexible container in accordance with the present invention having a hexagonal configuration showing the access port and the tubular access member; said tubular access member having the cap at the open end thereof, and luer slip stopcock assembly with vent positioned next to and adjacent to the access port.

FIG. 12 shows a hexagonal configuration of the pouch shown in FIG. 2 wherein the numeral 100' illustrates a logo in the shape of a hexagon embossed on one sheet of the pouch or attached to the outside wall of the pouch.

Figure 13A:
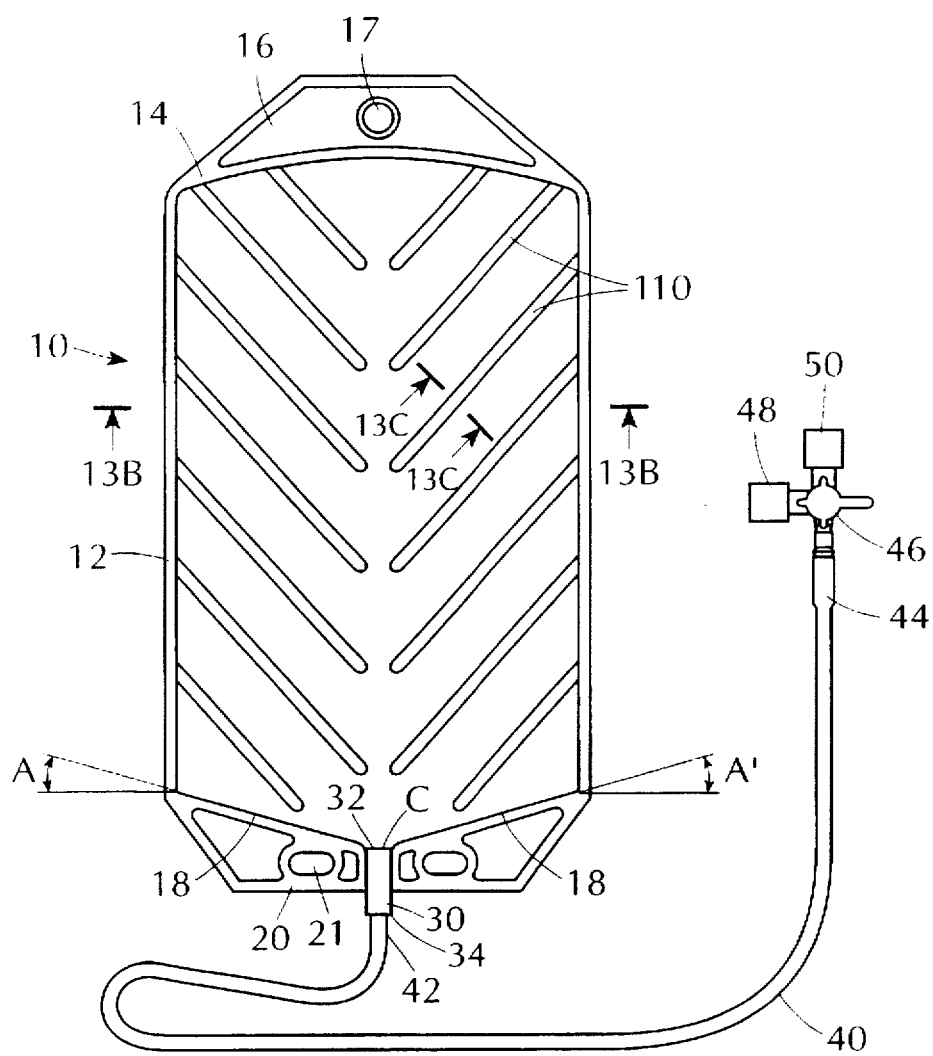
FIG. 13A is a plan view of the flexible container shown in FIG. 1 one wall of which is embossed with V-shape ribs.
Figure 13B:
FIG. 13B is a cross-section of the flexible container shown in FIG. 13A taken along the line 13B—13B.
Figure 13C:
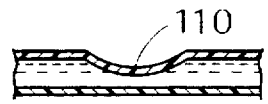
FIG. 13C is a cross-section of a rib on the flexible container shown in FIG. 13A taken along the line 13C—13C in FIG. 13B.

Referring to FIG. 13A, FIG. 13B and FIG. 13C, the inside wall of the first sheet is embossed with V-shaped ribs 110 of FIG. 1 in a spaced relationship from each other. The diameter of the width of individual ribs may be in the range of from about 0.01 to about 4.0 mms or larger, and preferably of from about 0.1 to about 0.40 mm. The individual ribs may be spaced from each other of from about 15 to 25 mms. While both inside walls of the first sheet and second sheet may be embossed, it is preferred that only one inside wall of the first or second sheet be embossed. Also, it is to be noted, that while the ribs of the V-shaped configuration may be a complete V-shape wherein the sides meet in a sharp angle, it is preferred that the ribs forming the V-shape do not meet but have a small gap therebetween. It was observed that the preferred configuration provides for a better drainage during aspiration of the fluid from the flexible container.

Figure 14A:
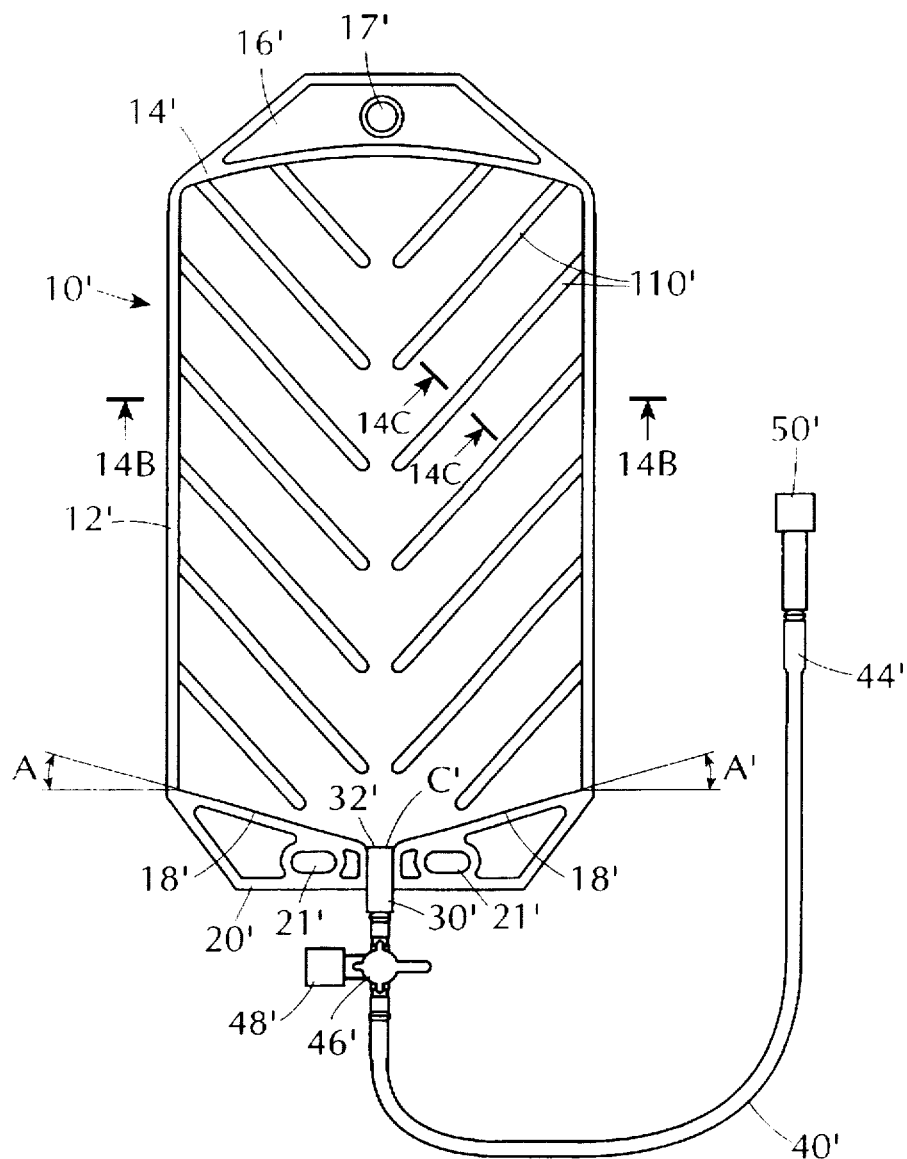
FIG. 14A is a plan view of the flexible container shown in FIG. 2 one wall of which is embossed with V-shape ribs.
Figure 14B:
FIG. 14B is a cross-section of the flexible container shown in FIG. 14A taken along the line 14B—14B.
Figure 14C:
FIG. 14C is a cross-section of a rib on the flexible container shown in FIG. 14A taken along the line 14C—14C in FIG. 14B.

FIG. 14A, FIG. 14B and FIG. 14C show the embodiment described in FIG. 2, except that the inside wall of the first sheet of pouch 10' is embossed with V-shaped ribs as described in FIGS. 13A, 13B and 13C.

Figure 15A:
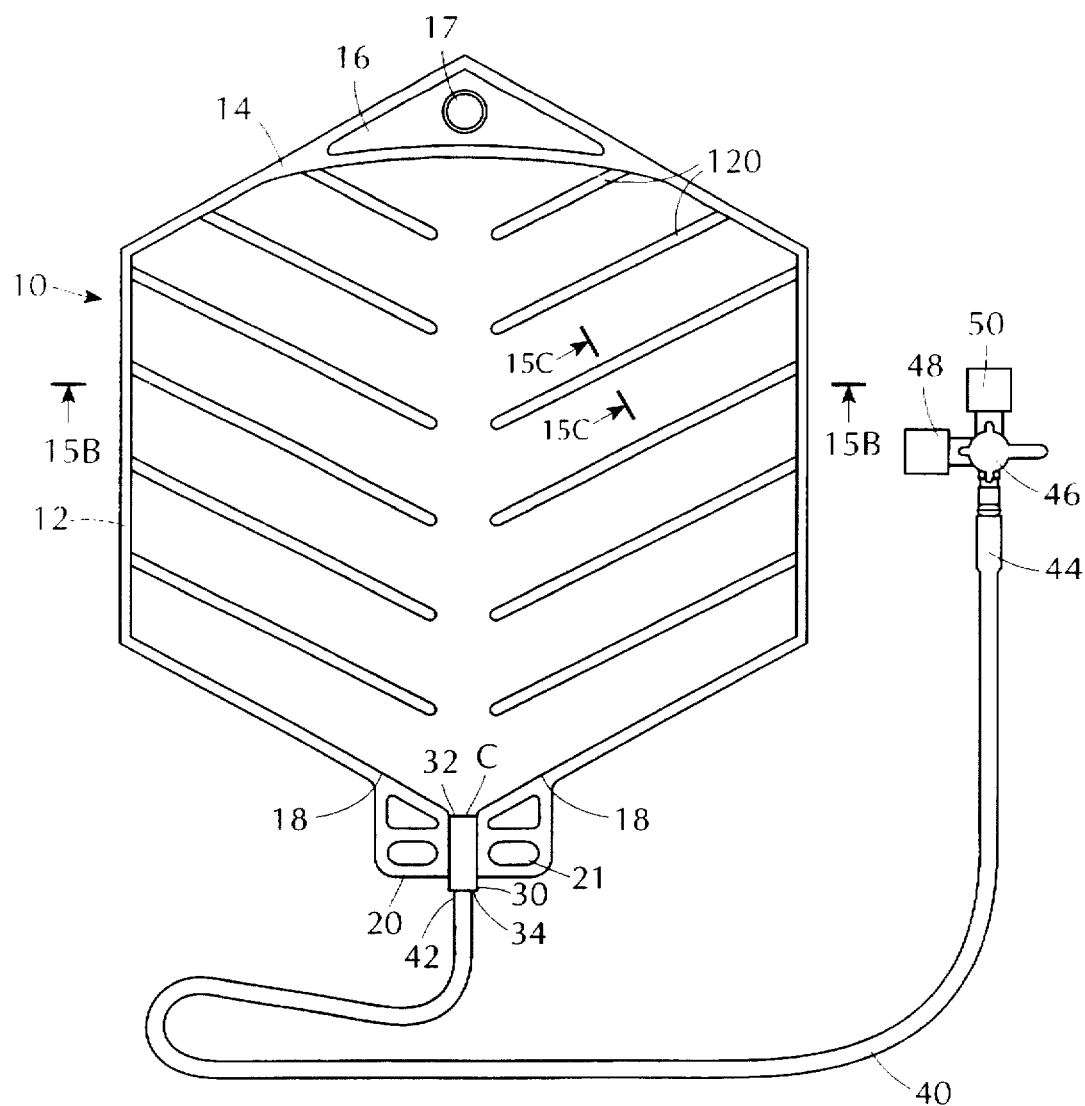
FIG. 15A is a plan view of the flexible container having a hexagonal configuration showing an access port, and a tubular access member; said tubular access member having a cap, and a luer slip stopcock assembly with vent at the open end of the access member; one wall of said flexible container is embossed with V-shape ribs.
Figure 15B:
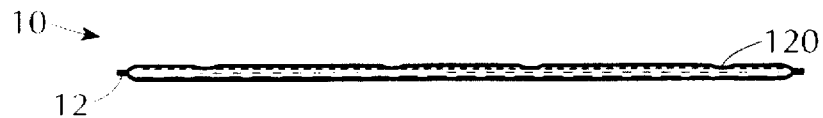
FIG. 15B is cross-section of the flexible container shown in FIG. 15A taken along the line 15B—15B in FIG. 15A.
Figure 15C:
FIG. 15C is a cross-section of a rib on the flexible container shown in FIG. 15A taken along the line 15C—15C in FIG. 15B.

FIG. 15A, FIG. 15B and FIG. 15C show a hexagonal configuration of the pouch shown in FIG. 1 wherein the inside wall of the first sheet is embossed with V-shaped ribs 120 in a spaced relationship from each other. The diameter of the width of the individual ribs and their spacing from each other are as described in FIGS. 13A, 13B and 13C.

Figure 16:
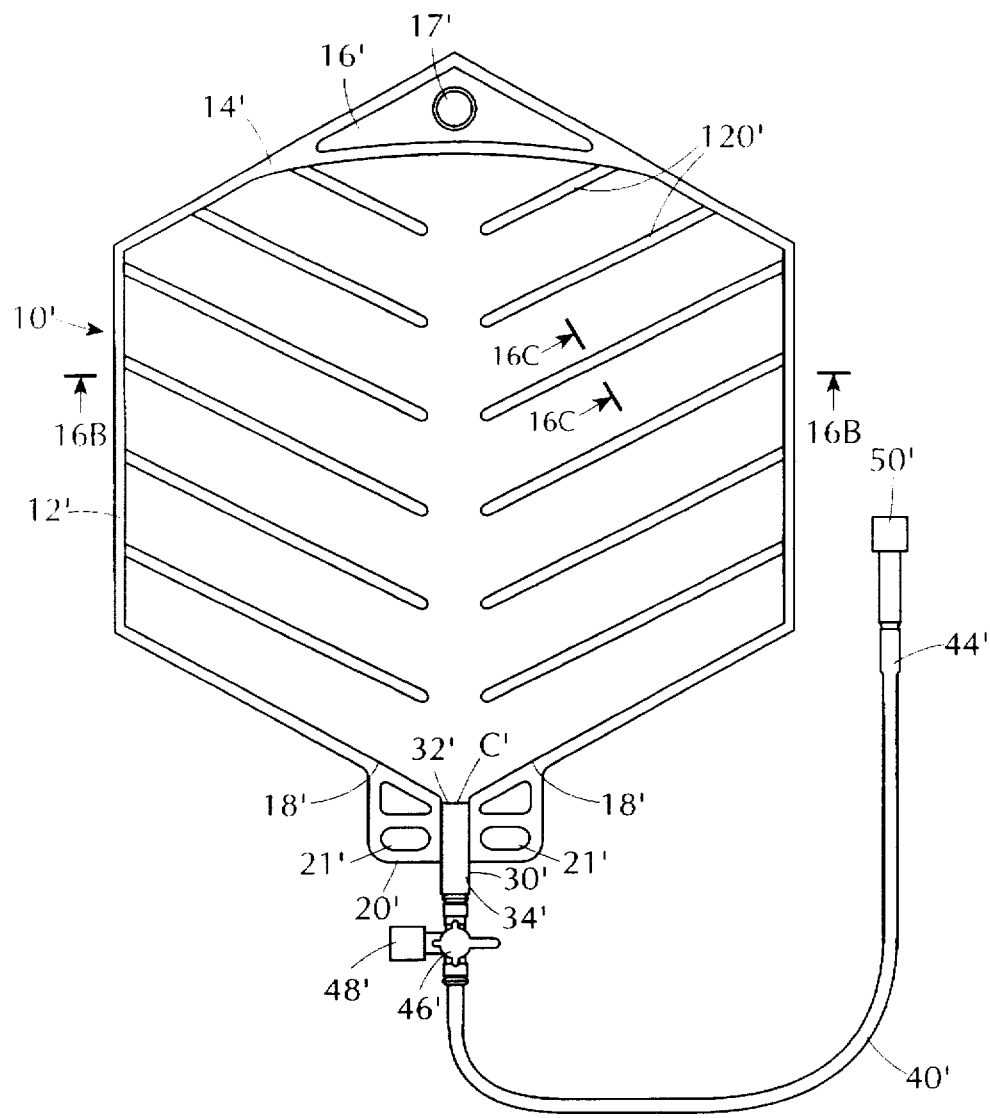
FIG. 16A is a plan view of the flexible container having a hexagonal configuration showing the access port and the tubular access member; said tubular access member having the cap at the open end thereof, and luer slip stopcock assembly with vent positioned next to and adjacent to the access port; one wall of said flexible container is embossed with V-shape ribs.
FIG. 16B is cross-section of the flexible container shown in FIG. 16A taken along the line 16B—16B in FIG. 16A.
FIG. 16C is a cross-section of a rib on the flexible container shown in FIG. 16A taken along the line 16C—16C in FIG. 16B.
Figure 16B:
Figure 16C:

FIG. 16A, FIG. 16B and FIG. 16C show a hexagonal configuration of the pouch shown in FIG. 2 wherein the inside wall of the first sheet is embossed with V-shaped ribs 120' in a spaced relationship from each other. The diameter of the width of the individual ribs and their spacing from each other are as described in FIGS. 13A, 13B and 13C.

Materials Of Construction

The flexible container of the present invention is made of known polymeric materials having properties which make them suitable for sterile delivery of parenteral liquids. The sheets for forming the walls of the container are monolayer, preferably multilayer, sheets and characterized by heat resistance, gloss, strength, flexibility, and chemical inertness. Preferably the sheets are transparent or at least translucent enabling visual inspection of the contents at all times during delivery of content from the container to the patient. The container must be sterilizable by dry heat, steam heat, irridiation (gamma), along with its content. At least one layer of the sheet provides a barrier to atmospheric gases and to steam. Preferably, the internal surface of the pouch in contact with the parenteral solution should be impervious to gases and steam. The interior layer in contact with the parenteral solution must not contain any toxic agents or even plasticizers which could leach out and contaminate the solution. The sheet may be made, for example, from polyvinyl chloride sandwiched between two polyethylene or polyvinylacetate layers. The polyvinyl chloride constitutes the impervious barrier. Further layers may be added to the face or back of the sheet, if desired, such as a polyolefin, preferably, polyethylene. Polyvinyl chloride is also suitable for the construction of the sheet and is well-accepted by the prior art for use in containers for medical fluid collection and delivery. Typical properties of polyvinyl chloride films include: a thickness of about 380 micron; a tensile strength of about 240 kg/cm$^2$; a moisture vapor transmission rate of about 14–20 (g/m$^2$/day at 38° C., 100% RH); and an oxygen barrier of 650 (cc/m$^2$/day at 23° C., 0% RH, bar. CRYO-VAC® sterlizable medical films (W. R. Grace and Co.) are especially suitable to construct the sheets used in the present invention. The films may comprise a polyethylene layer sandwiched between polyester outer layers sealed together by a modified propylene copolymer. Typical properties of the film include: a thickness of about 190 micron; a tensile strength of about 250 kg/cm$^2$; a moisture vapor transmission rate of 5 (g/m$^2$/day at 38° C., 100% RH); and an oxygen barrier of about 1500 (cc/m$^2$/day at 23° C., 0% RH, bar).

Other preferred polymeric films or sheets for constructing the flexible container of the present invention include: copolyester ether monolayer or multilayer films, manufactured from such as polycyclohexanedimethylcyclohexane dicarboxylate elastomer made by Eastman Chem. Co.; and ethyl vinyl acetate made by Stedim, Inc. It is important that the fluid contacting layer of the multilayer sheet contain no plasticizer which may contaminate the fluid content of the container. Preferably, no plasticizer should be used at all on any of the multilayers to form a flexible container of the present invention.

The sheets used in the present invention are embossed with the described configuration by techniques known in the art. Alternatively, the layer constituting the internal liquid contacting layer of the sheet may be embossed prior to forming the multilayer sheets.

Access port and tubing used in the present invention may be made of polyvinyl chloride which are sold commercially for use in medical devices. Other port and tubing materials may also be used, such as CRYOVAC® Port Tubing (W. R. Grace & Co.) which comprise three concentric layers of polymeric materials: a polyolefin layer is sandwiched between an outer layer of modified propylene copolymer and an inner layer of ethylene vinyl acetate or polyvinyl chloride.

Process Of Making The Container

The flexible plastic container in the form of a bag, pouch or bottle is made of two rectangular sheets of polymeric materials one of which is embossed and flat welded together on four sides so as to define between the two sheets and the four welded sides a reservoir. The volume of the container is zero before it is filled and typically has an internal volume capacity of from about 200 to about 1,000 ml when it is filled with a medical fluid, such as a parenteral solution. The access port 30 or 30' is sealed by the same welding process used to seal the two superimposed layers of sheets together at the center C or C' of the container 10 or 10'. Upon completion of the welding process the container is suspended via holes 21 or 21', followed by filling the container through the port with the desired medical fluid. Tubing 40 or 40' is then sealed to port 30 or 30' thereby making the container "ready for use". Alternatively, the container may be sealed by heat welding at its four edges except at its center portion C or C' and filled with the desired medical fluid prior to sealing access port 30 or 30' between the superimposed sheets. In this alternative process, however, the port 30 or 30' and tubing 40 or 40' are welded together forming an integral access member comprising the port and tubing. With either process, the container of the present invention, when filled with the desired medical fluid, provides for instant delivery requiring no assembly of the container and access member.

In the process of delivering the medical fluid to a patent, the container 10 or 10' is suspended via hole 17 or 17', cap 50 or 50' is removed and a spike or similar means is engaged with end of tubing 40 or 40'. One way luer slip stopcock assembly is turned to open position thereby starting the flow of medical fluid from the container through the tubing and spike to the site of delivery on the patient. Vent 48 or 48' allows outside air to replace the drained medical fluid in the container so that fluid flow is steady and continuous. If discontinuation of fluid flow is desired, the one-way luer stopcock assembly is turned to the stop position.

Various modifications of the several embodiments disclosed will become apparent. This invention is intended to include such modifications to be limited only by the scope of the claims.

What is claimed is:

1. A unitary, flexible container made of a polymeric material for the containment and delivery of medical fluids comprising:

a) first and second polymeric sheets having a square, round, oval, hexagonal, octagonal or rectangular configuration superimposed and sealed together at their periphery defining an interior reservoir, said container having a top portion and a bottom portion;

said bottom portion terminates in a first angle and a second angle of from about 5° to about 45° each from the center thereof and relative to a horizontal plane crossing the center of said bottom portion;

portions of said interior reservoir being mechanically or chemically embossed with ribs having a V-shaped configuration to maintain the polymeric sheets forming said interior reservoir spaced apart from each other thereby allowing relative movements of said polymeric sheets and preventing sticking therebetween;

b) an access member integral with said container located at the center of said bottom portion allowing filling of the container with a medical fluid and access thereto for delivery to a patient, said access member comprising:
        an access port located below the bottom portion of said container where said first angle and said second angle meet;
        a flexible tubing having first end and second end, said first end is integral with said access port and said second end is removably covered with a cap, said flexible tubing equipped with a one-way luer slip stopcock assembly with a vent for controlling the delivery of the medical fluid from the container.

2. The unitary, flexible container of claim 1, wherein said one-way luer slip stopcock assembly is located at said second end of said flexible tubing adjacent to said cap.

3. The unitary, flexible container of claim 1, wherein said one-way luer slip stopcock assembly is located at said first end of said flexible tubing adjacent to said access port.

4. The unitary, flexible container of claim 1 wherein the diameter of said ribs in said V-shaped configuration is of from about 0.01 to about 10 millimeters and said ribs are spaced from each other at a distance of from about 15 to about 25 millimeters.

5. The unitary, flexible container of claim 1 wherein said bottom portion terminates in a first and a second angle of from about 10° to about 30° each from the center thereof and relative to a horizontal plane crossing the center of said bottom portion.

6. The unitary, flexible container of claim 1 wherein said bottom portion terminates in a first and a second angle of from about 10° to about 20° each from the center thereof and relative to a horizontal plane crossing the center of said bottom portion.

7. The unitary, flexible container of claim 1 wherein said container further comprises at its top portion a heat welded periphery housing a hole therein for suspending said container during the filling process.

8. The unitary, flexible container of claim 1 wherein said container further comprises at its bottom portion a heat welded periphery having a plurality of holes therein for suspending said container during delivery of content to the patient.

9. The unitary, flexible container of claim 1 wherein said first and second polymeric sheets are made of polyvinylidene chloride sandwiched between two layers of polyethylene or polyvinylacetate.

10. The unitary, flexible container of claim 1 wherein said first and second polymeric sheets are made of polyvinyl chloride.

11. The unitary, flexible container of claim 1 wherein said first and second polymeric sheets are made of a polyethylene layer sandwiched between polyester outer layers sealed together by a propylene copolymer.

12. The unitary, flexible container of claim 1 wherein said first and second polymeric sheets are made of polycyclohexanedimethylcyclohexane dicarboxylate.

13. The unitary, flexible container of claim 1 wherein said first and second polymeric sheets are made of ethyl vinyl acetate.

* * * * *